US006867865B2

(12) United States Patent
Vaupel

(10) Patent No.: US 6,867,865 B2
(45) Date of Patent: Mar. 15, 2005

(54) SPR SENSOR

(75) Inventor: Matthias Vaupel, Göttingen (DE)

(73) Assignee: Nanofilm Technologie GmbH, Göttingen (DE)

( * ) Notice: Subject to any disclaimer, the term of this patent is extended or adjusted under 35 U.S.C. 154(b) by 163 days.

(21) Appl. No.: 10/258,028

(22) PCT Filed: Apr. 13, 2001

(86) PCT No.: PCT/DE01/01451

§ 371 (c)(1),
(2), (4) Date: Mar. 26, 2003

(87) PCT Pub. No.: WO01/79817

PCT Pub. Date: Oct. 25, 2001

(65) Prior Publication Data

US 2003/0164947 A1 Sep. 4, 2003

(30) Foreign Application Priority Data

Apr. 20, 2000 (DE) .......................................... 10019359

(51) Int. Cl.[7] .............................................. G01N 21/55
(52) U.S. Cl. ..................................................... 356/445
(58) Field of Search ........................................ 356/445

(56) References Cited

U.S. PATENT DOCUMENTS 5,926,284 A * 7/1999 Naya et al. ................. 356/445
6,577,396 B1 * 6/2003 Naya .......................... 356/445

FOREIGN PATENT DOCUMENTS

EP 0 577 285 A 1/1994

OTHER PUBLICATIONS

S. Shen et al., Optical Phase–Shift detection of surface plasmon resonance, Apr. 1, 1998, Applied Optics, vol. 37, No. 10, pp. 1747–1751.*
V. Vaicikauskas et al.: Leth. Phys J., vol. 39, No. 4, 1999, pp. 263–272, XP001017808.
S. G. Nelson et al.: Sensor and Actuators B, vol. 35, 1996, pp. 187–191, XP004049753.
A. A. Kruchinin and Yu. G. Vlasov: Sensors and Actuatros B, vol. 30, 1996, pp. 77–80, XP000584898.

* cited by examiner

Primary Examiner—Michael P. Stafira
Assistant Examiner—Juan D Valentin
(74) Attorney, Agent, or Firm—Birch, Stewart, Kolasch & Birch, LLP

(57) ABSTRACT

SPR sensor, in particular for detection of a layer of material, essentially consisting of a source for coherent monochromatic electromagnetic waves, a medium with a tunable index of refraction, and an imaging detection system, wherein the medium is designed as an optical resonator that has a first and a second opposing end face, upon each of which is applied at least one coating that is suitable for producing surface plasmon resonances, and wherein the imaging detection system has a polarization device and is designed such that at least one ellipsometric quantity produced by the SPR sensor in the reflected part of the incident coherent monochromatic electromagnetic wave can be detected.

27 Claims, 4 Drawing Sheets

SPR SENSOR

Figure 1:
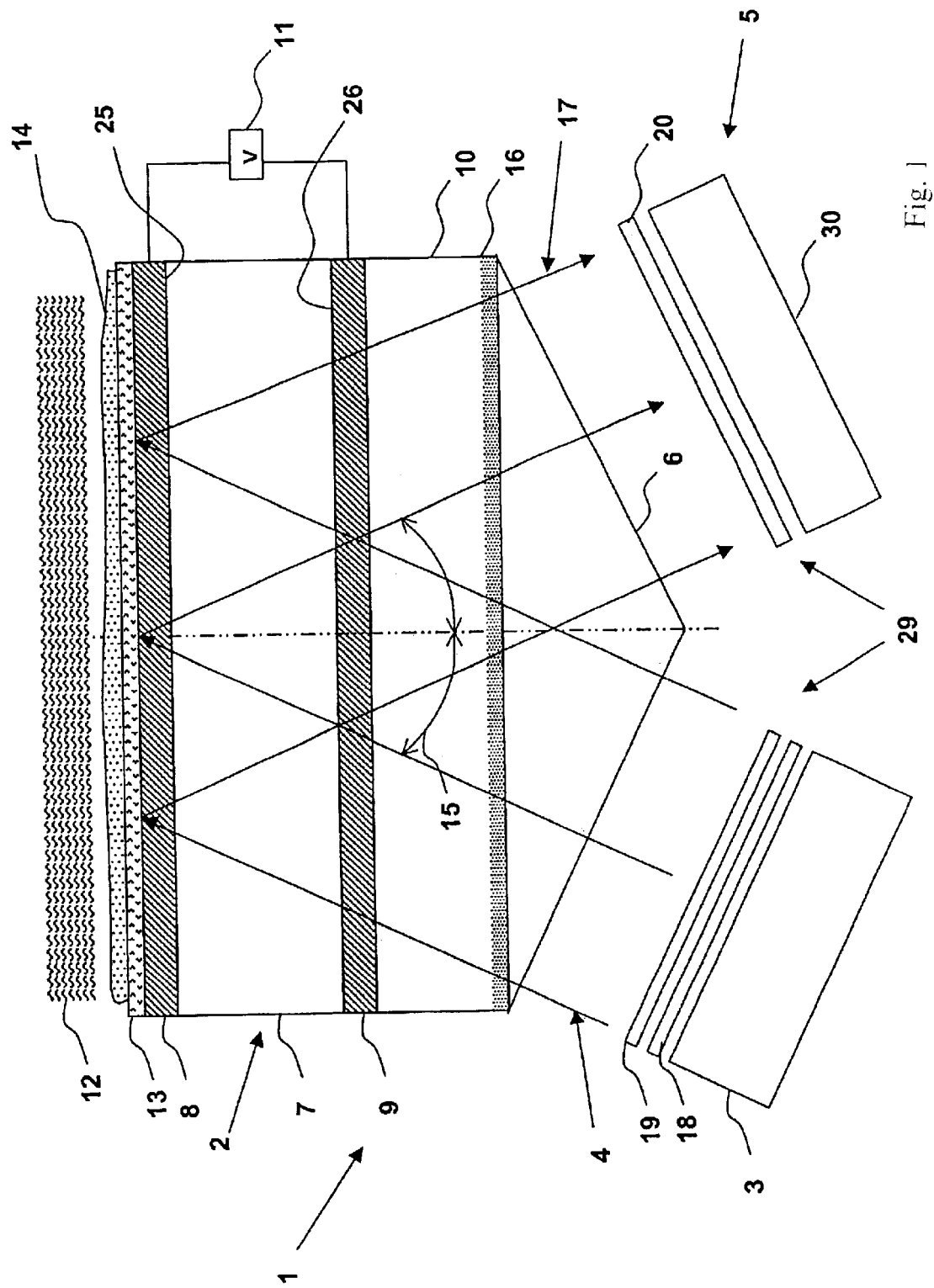

This application is the national phase under 35 U.S.C. § 371 of PCT International Application No. PCT/DE01/01451 which has an International filing date of Apr. 13, 2001, which designated the United States of America.

The invention relates to an SPR sensor, in particular for detection of a layer of material, essentially consisting of a source for coherent monochromatic electromagnetic waves, a medium with a tunable index of refraction, and an imaging detection system.

It is known to use SPR sensors (SPR stands for surface plasmon resonance) to measure changes in layer thickness and changes in the index of refraction in thin layers. They are used particularly in biochemistry as supersensitive detectors for investigating chemical reactions.

Surface plasmons are oscillations of the freely mobile electrons in the conduction band of electrically conductive solids, such as gold, under the influence of an external electromagnetic field. In this context, a compression or rarefaction of the electron gas occurs at the surface of the solid as a function of the polarity of the field. A periodic space charge pattern is produced whose interaction with the applied electric field causes the electron gas to oscillate at a resonant frequency known as surface plasmon resonance.

A prerequisite for the occurrence of surface plasmon resonance is that the wave vector and energy of the impinging electromagnetic wave coincides with the wave vector of the surface plasmons. The wave vector of an electromagnetic wave is given by $k_e=(\omega/c) n \sin\Theta$, where $\omega$ is the angular frequency of the incident wave, c is the speed of light, n is the index of refraction, and $\Theta$ is the angle of incidence. The wave vector of the surface plasmons is defined by $k_s=(\omega/c)(1/\epsilon_m+1/\epsilon_s)^{-1/2}$. Here, $\epsilon_m$ and $\epsilon_s$ are the dielectric constants of the conductive solid, such as a thin metal layer, and a substance to be investigated which has been deposited on the solid, such as a reaction product. Use of surface plasmon resonance in an SPR sensor is described, for example, in Kretschmann (Opt. Comm. 6 (2), p. 185 ff, 1972): a coherent p-polarized wave passes at the angle of total reflection from an optically dense medium with refractive index $n_1$ into an optically rarefied medium with refractive index $n_2 < n_1$. The boundary in this case is coated with a thin metal film in which the wave is damped. For suitable parameters (angle of incidence, wavelength, refractive index), the wave vector matches the resonant frequency of the surface plasmons and excites them into oscillation. In the ideal case, all of the incident energy is absorbed to maintain the oscillation, which means a complete suppression of the total reflection.

Moreover, ellipsometry is known as a measurement method for studying surfaces and thin films. Ellipsometry is a special form of reflection spectrometry that deals with the change in the polarization state upon the reflection of polarized light at a surface. Its advantages reside in the nondestructive measurement technique and its high sensitivity, which permit measurements into the submonolayer region in atoms and molecules. Moreover, ellipsometry is an absolute method, i.e., no calibration standards are required. Ellipsometric analysis yields the optical constants, namely the refractive index n and the absorption coefficient k. In layer systems, it is also possible to determine the layer thickness d.

The fundamental equations of ellipsometry were formulated as early as the beginning of the last century. When polarized light strikes a plane surface, both the amplitude and the phase of the parallel and perpendicular vector components of the electric field change. The component whose electric field vector lies parallel to the plane of incidence is called p-polarized, and the component whose electric field vector is perpendicular to the plane of incidence is called s-polarized. The resulting polarization state is usually elliptical, hence the name "ellipsometry". The measurement method of ellipsometry makes it possible to measure this ellipse and determine the phase difference $\Delta=\delta_p-\delta_s$ and also the relationship of the amplitudes $\tan\psi=|r_p|/|r_s|$.

In standard devices for layer thickness measurement (such as those made by the Biacore company), SPR is excited through reflection of p-polarized light from an SPR-capable metal layer. The change in reflection in this case indicates a change in the thickness of the layer deposited on the metal (especially through chemical binding or adhesion). The resolution of the layer thickness in this method is determined by derivation of the coefficients of reflection in accordance with the layer thickness.

Alternatively, ellipsometry can be performed on the layer system. In this case, the ellipsometric quantities $\Delta$ and $\psi$ are measured (R. M. A. Azzam and N. M. Bashara, "Ellipsometry and Polarized Light," North Holland Physics, 1987). $\psi$ is proportional to the reflection coefficient of the p-polarized light, and hence recovers the same thickness resolution as the reflection coefficient itself. In contrast, the derivative of the phase shift $\Delta$ in accordance with the layer thickness is theoretically unlimited. It is determined by metal or adsorbate layer thickness and wavelength. The sensitivity as compared to conventional SPR devices can be increased by measuring $\Delta$ (E. G. Bortchagovsky, "Possibilities of ellipsometry with the surface plasmon excitation in the investigation of thin films in comparison with separated ellipsometry and surface plasmon spectroscopy in Polarimetry and Ellipsometry," Maksymilian Pluta, Editor, Proc. SPIE 3094, 239 (1997)).

Conventional SPR sensors can only work at a certain angle of incidence, for example 75° in the case of the gold/glass system with a refractive index of n=1.52. This represents a problem, in particular in the parallel detection of multiple detection channels using imaging SPR detection or imaging ellipsometry, since the surface of the sensor is imaged in a distorted fashion when the beam is not incident perpendicular to the surface of the input optics, generally a prism (Hoenig, Optoelectr. World, p. 37, October 1998). A system-induced deviation from the perpendicular angle of incidence thus causes reduced sensitivity and measurement accuracy.

Moreover, in practice sensitivity is limited by manufacturing tolerances of the metal layer and the varying thickness in situ of the deposited biochemical layer.

These tolerances can be compensated in the case of a single-channel SPR sensor through tuning the wavelength of the light used (K. Johansen, H. Arwin, I. Lundstrom, B. Liedberg, "Imaging surface plasmon resonance sensor based on multiple wavelengths: Sensitivity considerations," Rev. Sci. Instr. 71, 3530 (2000)). However, this is impractical on account of the high prices for such tunable light sources. Moreover, the sensitivity of the SPR cannot simultaneously be optimized in all pixels of an SPR array in this way.

In order to satisfy the increasing demands on nanotechnology, it is necessary to precisely measure very thin layers in the range from 50 nm to less than 1 pm as well as complex refractive indices of layers or of a surrounding medium with microscopic spatial resolution. In this case, the measurement should, if possible, be performed simultaneously at various layer locations. Moreover, a simultaneous measurement of refractive index and layer thickness should also be possible for the aforementioned very thin layers. To date the known ellipsometry can only accomplish this for thin layers with substrates matched to the individual layer.

Known from U.S. Pat. No. 5,351,127 is an SPR sensor that has a medium with an index of refraction that can be varied through the application of an electrical voltage. The medium has at an end face a metal coating upon whose surface is located a sample to be investigated. Under appropriate conditions, surface plasmons are generated at the surface (metal layer/material layer) of the sensor by irradiation with an electromagnetic wave, for example by means of a laser diode. The resonances can be detected with a detector, for example a diode array, by measuring the intensity of the reflected wave. Changes in the material layer cause a change in the resonance condition for generating surface plasmons. The intensity measured at the detector changes accordingly.

Although this arrangement can in theory improve the sensitivity of the sensor by tuning the index of refraction, no material with a suitably large change in refractive index is available.

A particular disadvantage with this arrangement is that surface plasmon resonances can only be generated in a very small range of angles of incidence of the electromagnetic wave. This results in limited usability, especially for imaging detection methods, since an SPR sensor can only be optimally operated with an imaging detection method when the angle of incidence of the incident electromagnetic wave at the input optics is perpendicular. However this is not easily possible with the known device.

Another disadvantage is that detection is performed exclusively by measuring the intensity of the reflected wave, with the result that the sensitivity of the sensor is relatively low.

A tunable surface plasmon filter is known from U.S. Pat. No. 5,986,808. The filter has a dielectric layer, made for example of liquid crystals, both end faces of which are provided with metal layers, and which together form an optical resonator. The resonance can be influenced by applying a voltage or changing the thickness of the dielectric layer. In order to change the spectral composition of an incident wave, white light is used as the incident wave. The reflected or transmitted light then does not contain the wavelengths that fulfill the resonance condition, or contains them only with sharply attenuated intensity. The filter effect with respect to the colors can be changed by varying the index of refraction.

A disadvantage of this filter is that white light that is filtered by the SPR effect is used as the incident wave. Yet this light is not suitable for an SPR sensor for investigating material layers, since the fullest possible absorption of the incident wave is important here. Nor is the application of a layer of material easily possible. Moreover, no detection system is provided. The known filter thus cannot be used to improve an SPR sensor for material layer investigation.

From U.S. Pat. No. 5,451,980 is known a flat panel color display whose principle of operation is based on the wavelength-selective scattering of white light by the excitation of surface plasmons. This device has a liquid crystal layer of which one end face is provided with a metal coating. A matrix of a plurality of individual electrodes is arranged at the second end face of the LC layer. Alternatively, the metal layer can also be replaced by a second electrode matrix.

The color composition of the scattered light can be varied by means of a color modulator which is electrically connected at one end to the metal layer through a conductive contact and at the other end with the matrix of (transparent) electrodes. The resonance condition for surface plasmons can be sequentially varied for each pixel of the display in order to assign it (the pixel) a specific color. No provision is made for detection of the colored pixel generated by means of the matrix.

A disadvantage is that white light is used here also as the incident wave in order to generate scattered light with specific spatially resolved color properties. The application and detection of a material layer is not possible. The device thus likewise cannot be used for an SPR material layer sensor.

The object of the present invention is thus to develop an SPR sensor for investigating a material layer that has high sensitivity and accuracy of measurement, and in which the angle of incidence of the incident radiation can be freely selected over a wide range of angles.

The object is achieved in accordance with the invention in conjunction with the preamble to claim 1 in that the medium is designed as an optical resonator that has a first and a second opposing end face, upon each of which is applied at least one coating that is suitable for producing surface plasmon resonances, and in that the imaging detection system has a polarization device and is designed such that at least one ellipsometric quantity produced by the SPR sensor in the reflected part of the incident coherent monochromatic electromagnetic wave can be detected.

Since the resonances of an optical resonator occur at regular angular intervals and each of these resonances can be used as SPR, it is typically possible to choose the angle of incidence of the SPR in the range $45°<\Theta<90°$. In particular, the electromagnetic wave can thus always be coupled into the input optics in a perpendicular or nearly perpendicular direction. This produces no image distortion with imaging detection methods, which is especially advantageous for the parallel detection of multiple detection channels by means of imaging ellipsometry.

Conventionally, the reflection of p-polarized light at the SPR sensor, which is proportional to the ellipsometric $\psi$, is detected. The angle of incidence there is chosen on the edge of the resonance in order to measure a shift in the resonance using the changed reflection of the light. The sensitivity here is determined by the steepness of the edge. The steepness is determined by the optical characteristics of the sensor materials used and is limited thereby. In contrast, if one uses the ellipsometric $\Delta$ for layer thickness measurement, the sensitivity is further increased: the $\Delta$ behaves as the derivative of $\psi$. Hence its slope is greatest at the resonance angle. In particular, the slope can (theoretically) approach infinity when $\psi$ reaches zero at the minimum.

According to a preferred embodiment of the invention, the imaging detector system is designed such that an ellipsometric phase shift generated by the SPR sensor in the reflected part of the incident electromagnetic wave can be detected. The detector system can be designed such that even a change in amplitude, i.e. the change in the amplitude relationship of the parallel and perpendicular vector components of the electric field, can be detected before and after reflection at the sensor.

While the analysis of the ellipsometric phase shift increases the sensitivity of the sensor, the simultaneous measurement of the ellipsometric quantities $\Delta$ and $\psi$ in the vicinity of the SPR permits the index of refraction n and layer thickness d to be determined simultaneously, thereby improving the effectiveness of the sensor.

In accordance with another preferred embodiment of the invention, an optical component is provided for coupling the coherent monochromatic electromagnetic waves into the medium.

Preferably the incident wave is coupled into the resonator through an optical component, e.g. a prism of silica glass.

In accordance with another preferred embodiment of the invention, the resonator is arranged on an object holder suitable for coupling coherent monochromatic electromagnetic waves into the resonator.

The object holder is preferably made of glass. An optical component may be situated in front of it. This arrangement simplifies handling of the sensor and protects it from damage.

In accordance with another preferred embodiment of the invention, the polarization state of the electromagnetic wave can be adjusted with polarization means by the polarization device.

The polarization device preferably uses a polarizer and an analyzer, e.g. special filters, for polarization and analysis of the polarization state before and after the interaction of the incident radiation with the sensor or the material layer. By means of additional polarization means, such as a compensator, for example in the form of a $\lambda/4$ plate, the polarization phase can be set and altered. This is particularly advantageous with the technique known as null ellipsometry, in which the change in the polarization state is compensated for by a compensator. The analyzer is then rotated to adjust to a radiation minimum. Finally, the ellipsometric quantities can be determined from the angular settings of the compensator and analyzer. Very high measurement accuracy of the detector system and the SPR sensor is achieved in this way.

In accordance with another preferred embodiment of the invention, the electromagnetic wave has a wavelength that can be predetermined.

As a result of the fact that wavelengths from a very wide wavelength range, i.e. from the ultraviolet to the infrared, can be used, there is very great flexibility in constructing the SPR sensor from various suitable materials and also in suitability for detection of various substances.

In accordance with another preferred embodiment of the invention, the material layer to be detected can be applied to either of the two end faces of the resonator as desired.

This permits flexible use of the resonator, in particular the coupling in of the incident radiation from the upper or lower side.

In accordance with another preferred embodiment of the invention, it is possible to apply to the end faces of the resonator at least one indicator substance upon the surface of which can be formed a material layer to be detected through reaction with an ambient medium. A reaction cell may also be provided in which a material layer can form in a liquid or gaseous environment.

With the aid of an indicator substance, a material layer to be investigated can form on the sensor through reaction with an ambient medium. Of course, multiple indicator substances may also be used. In the process, multiple reaction products can form, which can be investigated simultaneously with the SPR sensor. For simple operation it is beneficial to use a reaction cell for introducing an ambient medium in order to produce a specific material layer.

In accordance with another preferred embodiment of the invention, the coating on the end faces of the resonator consists of electrically conductive layers. A coating of a layer system of conductive and nonconductive layers is possible as well.

As a result of the various coating possibilities, the SPR sensor can be used for a great variety of substances. In particular, a layer system of conductive and micrometer-thin nonconductive layers is suitable for compensating for manufacturing tolerances in the metal coating thicknesses, in order to further increase the sensitivity in this way. A resonator constructed in this way can thus further improve the SPR sensor.

In accordance with another preferred embodiment of the invention, the medium of the resonator consists of a material with nonlinear electrical or magnetic susceptibility.

Such nonlinear materials are especially well suited for determining the index of refraction using light.

In accordance with another preferred embodiment of the invention, the medium consists of an electro-optical polymer or an electro-optical crystal.

These materials are especially well suited for determining the index of refraction in optical resonators of SPR sensors.

In accordance with another preferred embodiment of the invention, the medium consists of an elasto-optical material.

Elasto-optical materials react to the action of external mechanical forces with a change in refractive index. As a result of the possibility of exerting external mechanical forces on the medium, materials of this nature are thus suitable for tuning the refractive index in SPR sensors. Moreover, these materials can be used to advantage in resonators made of layer systems.

In accordance with another preferred embodiment of the invention, an electric field can be applied to the medium in order to adjust the index of refraction.

As a result of the fact that the index of refraction can be adjusted by an electric field, the SPR sensor using electro-optical resonator media can be operated continuously at high sensitivity during a measurement by tuning the voltage during a change in the layer thickness or refractive index to be detected.

In accordance with another preferred embodiment of the invention, the index of refraction in the medium can be adjusted on the basis of a nonlinear optical effect through the intensity of an electromagnetic modulation beam that is additional to the coherent monochromatic electromagnetic wave and enters at an arbitrary angle of incidence.

The refractive index of the electro-optical medium is varied by means of a modulation device that has a modulating beam. Preferably the modulating beam is implemented as a laser beam and has diverging optics. Tuning of the resonator, or of microresonators implemented as separate cells, is accomplished through (spatial) intensity modulation of the modulating beam (achieved as needed by a liquid crystal display or a digital mirror device or a digital light projector). In the case of certain electro-optical media, a bias voltage is additionally used to advantage in order to achieve sufficiently large refractive index changes. This permits especially high resolution refractive index tuning.

In accordance with another preferred embodiment of the invention, the SPR sensor is distributed among separate cells, microresonators, which can be excited, tuned or detected individually or together, as desired. In this way it is possible to register in parallel multiple detection channels of the layer or layers to be detected by means of imaging ellipsometry and simultaneously to operate each individual sensor cell with high sensitivity. In this way, the sensor can be used especially effectively in biotechnology to investigate various material layers, such as protein spots.

In accordance with another preferred embodiment of the invention, the medium of the resonator has a low extinction.

In order to achieve the highest possible sensitivity, the attenuation or amplification of the incident wave in the resonator should be as small as possible. Thus, a low extinction coefficient has a beneficial effect. Preferably, it should be at $|k|<0.1$.

Additional details of the invention are made evident by the detailed description below and the attached drawings, which illustrate preferred embodiments of the invention by way of example.

Shown in the drawings are:

FIG. 1: A side view in cross-section of an SPR sensor with an ellipsometric detection system and coupling of the incident beam from below through the resonator, FIG. 2: a side view in cross-section of a second embodiment of the SPR sensor with entry of the radiation from above onto the layer to be investigated in a reaction cell, FIG. 3: a side view in cross-section of another embodiment of the SPR sensor from FIG. 2 with a modulating beam, and FIG. 4: a function plot $\psi(\Theta)$ as the result of a computer simulation for optimizing the sensitivity of an SPR sensor.

An SPR sensor 1 for the detection of material layers 14, 14' consists essentially of a source 3 for coherent monochromatic electromagnetic waves 4, an optical resonator 2 with a medium 7 whose opposing end faces 25, 26 are each provided with a coating 8, 9, 9' suitable for producing surface plasmon resonances, SPR, and an imaging detection system 5 with a polarization device 29 for measuring ellipsometric quantities.

The coatings 8, 9, 9' of the resonator 2 are semitransparent gold layers. The medium 7 of the resonator 2 consists of an electro-optical polymer whose index of refraction n can be varied up to a factor of 0.01 by the application of an electric field through the metallic coatings 8, 9, 9' by means of a voltage supply 11, 11'. The resonator 2 with the coatings 8, 9, 9' has a thickness of approximately 2 to 10 wavelengths. It is applied to a glass object holder 10 a few millimeters thick, through which a laser beam 4 is coupled into and out of the resonator 2 by means of diverging optics (not shown) by means of an immersion oil 16 and an optical component 6, advantageously in the form of an ordinary commercial prism. A suitable polymer may also be used in place of the immersion oil 16. The laser beam 4 first passes through the resonator 2 to the sensor surface. In order to achieve high efficiency, the resonator medium 7, especially in this embodiment, has very low extinction, $|k|<0.1$. Of course, high sensitivity can also be achieved with optical amplification, such as in the form of a laser resonator, thus with negative extinction. In particular, absorption in the resonator 2 can be compensated for by optical amplification.

Adjustment of the detection system 5 is accomplished in accordance with the principle of null ellipsometry by compensation of the polarization change. In principle, photometric measurement without compensation is also possible, but is not discussed further here.

The detection system 5 has the polarization device 29 and a detector 30, advantageously in the form of a CCD camera with imaging optics (not shown). The detector 30 detects an area of the SPR sensor 1, also called pixel array, with high spatial resolution. The polarization is adjusted by a polarizer 18 located in front of the prism 6, together with a compensator 19. For example, the laser beam 4 is linearly polarized by the polarizer 18, advantageously in the form of polarization filter[s]. The subsequent compensator 19 with a phase shift of 90° is adjusted such that it compensates the change in the polarization state resulting from the reflection at the surface of a material layer 14, 14' formed on the resonator layer 8. The reflected light 17 is then linearly polarized again. An analyzer 20, advantageously designed as polarization filter[s] like the polarizer 18, now serves to determine the polarization state. Since the compensator 19 has again generated linearly polarized light, the analyzer 20 is adjusted by rotation to a radiation minimum. The ellipsometric measurement quantities $\Delta$ and $\psi$ can be determined from the angle settings of the compensator 19 and the analyzer 20.

The phase shift, in particular, reacts with extreme sensitivity to changes in wavelength, angle of incidence, refractive index and layer thickness. For example, a change in the layer thickness of the material layer 14, 14' can be measured through compensation of the change in refractive index of the resonator medium 7 in order to keep the phase shift $\Delta$ constant as the layer thickness changes.

To do so, first the incident wave 4 is adjusted by a suitable device (not shown) such that it enters the prism 6 approximately perpendicularly, by which means it is coupled into the resonator 2. The range of angles is then varied by a few degrees about the angle of incidence 15.

The optical resonator 2 has resonances at regular angular intervals. For a sufficiently large angle of incidence 15 (approximately $45°<\Theta<90°$), each of these resonances is a surface plasmon resonance. The surface plasmon resonances arise in the coatings 8, 9, 9' of the resonator. Thus, for a small angular variation of a few degrees of the laser beam 4 that is coupled perpendicularly into the prism 6, one finds at least one surface plasmon resonance which can be observed by a drop in intensity of the reflected intensity 17.

If a material layer 14, 14' has formed, for example through a chemical reaction of the indicator substance 13 with the ambient medium 12 (for example, water, DNA), a change in thickness or refractive index at the surface of the SPR sensor 1 can be measured by a change in the voltage required to keep the ellipsometric phase shift, which is measured as described above, constant.

The conversion of voltage change to change in thickness or refractive index can be undertaken in accordance With Azzam's theory of ellipsometry, for example (R. M. A. Azzam et. al., Ellipsometry and Polarized Light, Elsevier, Amsterdam, 1987).

Figure 2:
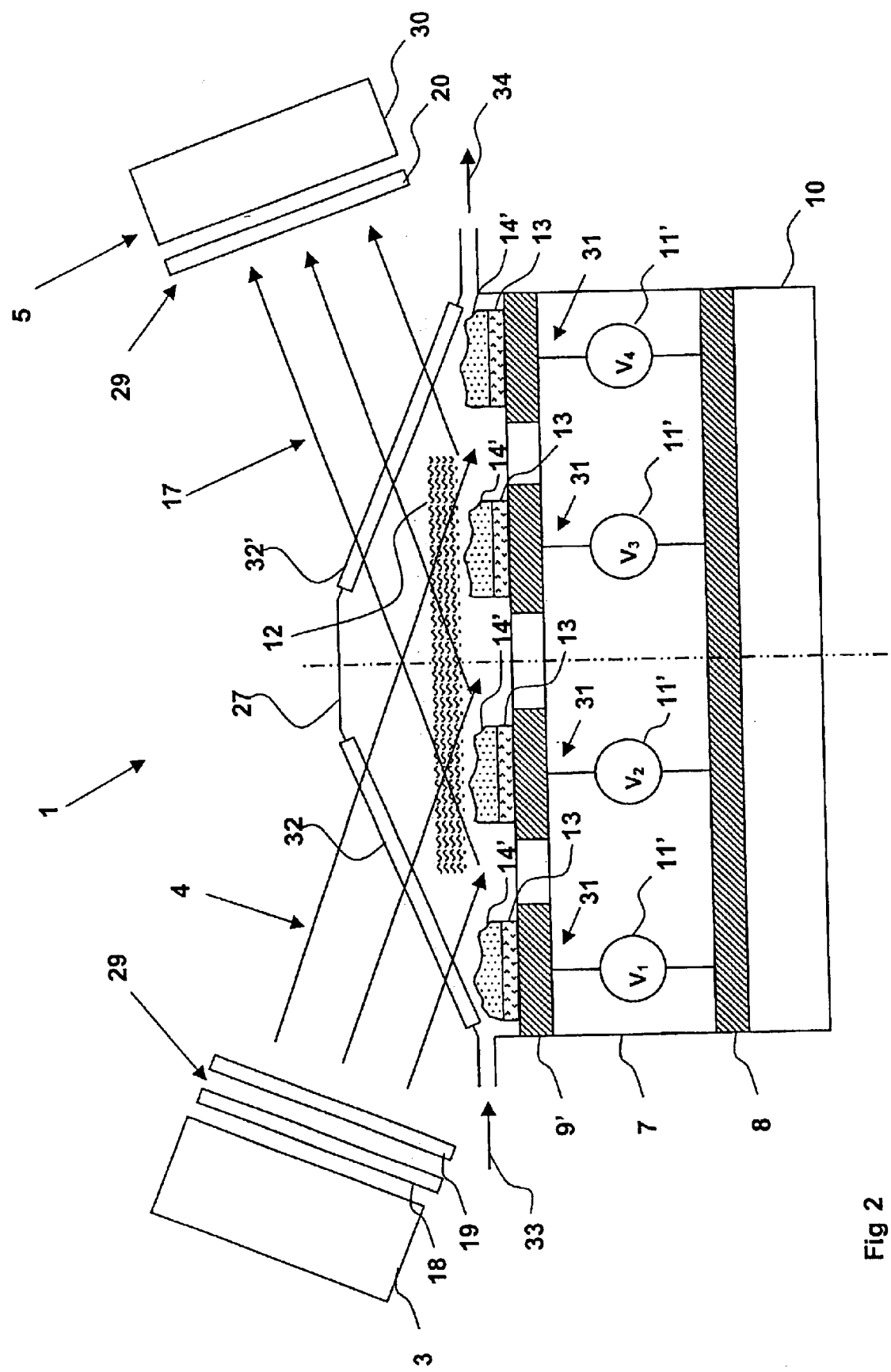
Figure 3:
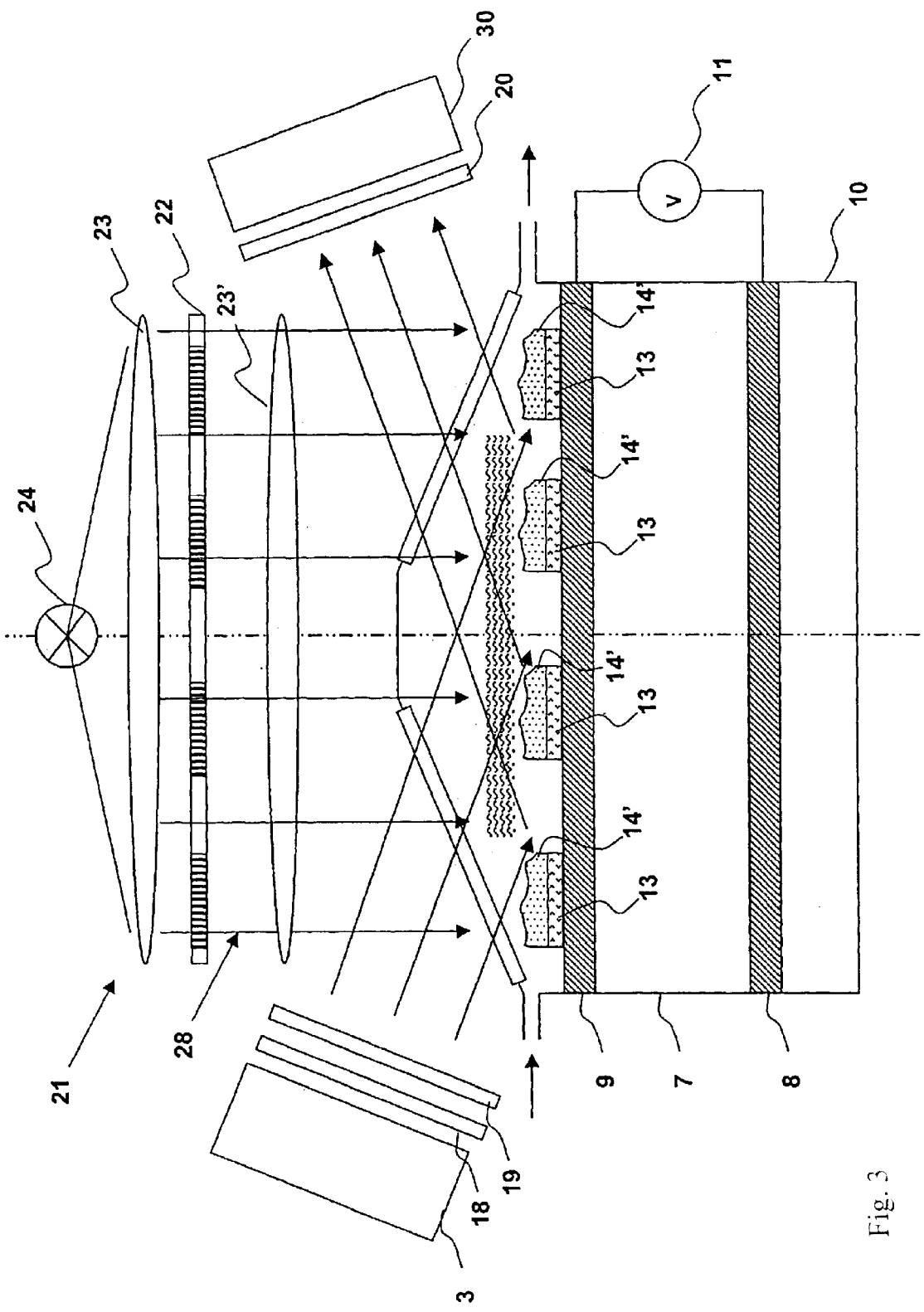

In a second embodiment, shown in FIG. 2, there is arranged on the resonator 2 a reaction cell 27 with an inlet 33 and an outlet 34 for an ambient medium 12 for indicating a reaction with an indicator substance 13. The medium 7 typically has a thickness of 2–10 wavelengths of the incident radiation 4. In this implementation, the laser beam 4 strikes the resonator 2 from above by means of diverging optics (not shown) through a cell window 32 of the reaction cell 27. The reflected beam 17 is imaged by imaging optics (not shown) and the analyzer 20 onto the camera 30. The upper semi-transparent metal layer 8 is spatially structured and is populated with various protein spots 14'. Consequently, a separate microresonator 31 that is tunable through its voltage 11' is located beneath each protein spot 14'. The SPR can thus be separately optimized for each spot 14'. It is also possible to determine the layer thickness by measuring the voltage $V_i$ (11').

In another embodiment (FIG. 3), a modulation device 21 performs the refractive index tuning. A modulating beam 28, advantageously in the form of a laser beam, is directed in from above, through diverging optics 23, 23'. Of course, the modulating beam 28 could also be directed into the resonator 2 from below. Tuning of the microresonators (separate cells) 31 is accomplished by this beam. In advantageous fashion, a bias voltage 11' is applied in order to achieve adequately large refractive index changes. The intensity of the modulating beam 28 is modulated spatially as it passes through a liquid crystal display 22 and a polarizer (not shown). The individual pixels of the display 22 are imaged on the microresonators 31. In this way the microresonators 31 are controlled by means of the voltage 11 applied to the pixels. In contrast to the embodiment in FIG. 2, this control of the microresonators 31 requires no structured metal layer 9'.

Since the SPR excitation depends primarily on the angle of incidence 15 and the refractive index, one can operate the SPR sensor 1 with high sensitivity by iteratively guiding the angle of incidence 15 and the index of refraction of the resonator medium 7 to an intensity minimum with p-polarized incident light. The refractive index of the resonator medium 7 can be adjusted by appropriately adjusting the applied voltage 11, 11'. The inflection point of the phase shift Δ the angle of incidence 15 at which the SPR occurs. The steepness of this phase shift Δ function of the angle of incidence 15 at the inflection point can be increased by adjusting the index of refraction as described above. This is synonymous with an increase in the sensitivity and the relative measurement accuracy of the SPR sensor.

An example in the form of a computer simulation for optimizing the sensitivity of an SPR sensor is presented below. Experimentally achievable conditions are assumed in this context.

Figure 4:
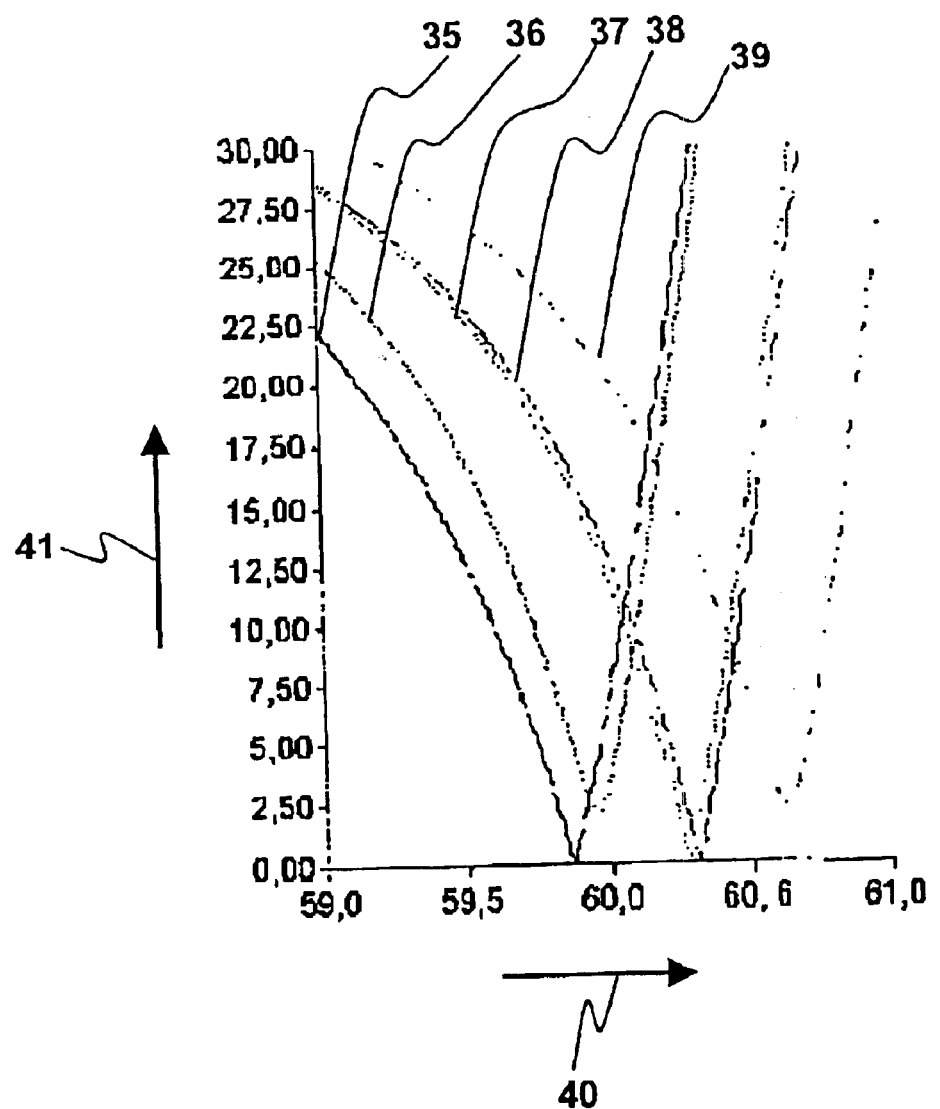

FIG. 4 shows the ellipsometric quantity ψ in the direction 41 as a function of the angle of incidence Θ in the direction 40 for various pairs of thicknesses d(Au)/d(poly) of gold layer and polymer medium. The values n(Au)=0.34 and n(poly)=1.7 were assumed as initial values for the refractive index.

The following systems were simulated:

| Reference Number | 35 | 36 | 37 | 38 | 39 |
|---|---|---|---|---|---|
| d(Au) [nm] | 16 | 17 | 17 | 17 | 17 |
| d(poly) [nm] | 1999 | 1999 | 2009 | 2010 | 2020 |

A change in thickness of a biochemical layer should be detected at the individual pixels of an SPR sensor. The SPR sensor consists of glass with gold (Au)/electro-optical polymer (EO)/gold layers. The thickness change to be detected on the SPR sensor causes an change in the angle at which the SPR (minimum in FIG. 4) occurs. A change in the gold or polymer layer thicknesses, or the wavelength, has a similar effect. The Δ acts as the derivative of ψ. Its slope is thus greatest at the resonance angle. In particular, the slope can theoretically approach infinity when ψ reaches zero at the minimum.

In order to illustrate optimization of the sensitivity, we proceed from the least favorable case, namely that the polymer thickness (assumed to be d(poly)=2010 nm) with no applied voltage makes the value of ψ(Θ) at its minimum as large as possible for an initially employed wavelength of 633 nm. In this case, d(poly) would have to be tuned by approximately 250 nm in order to bring the minimum to an angle of 0°. Changing the refractive index of the polymer by approximately Dn=0.1 or tuning the light wavelength to approximately 668 nm would achieve the same purpose. If we now assume the latter, the sensitivity of some of the pixels of the sensor could thus be optimized by means of the wavelength. Other pixels, in contrast, would not have optimum sensitivity because of local variations in thickness of the gold, polymer and biochemical layers on the sensor surface. However, these pixels can be optimized in their behavior through locally adjusting the refractive index of the polymer. Thus, a variation of 1 nm in the gold thickness, or of 10 nm in the polymer thickness, can be compensated by a change in refractive index Dn=0.004. This change in Dn can be achieved reliably with EO polymers.

Changes in layer thickness of the layer 14, 14' to be detected can be measured in this way in that the index of refraction is adjusted during the layer growth such that the reflection remains constant. In particular, the layer thickness can be determined by changing the applied voltage 11, 11'.

Of course it is possible to perform the measurement of the layer thickness of all pixels in that the refractive index of the resonator medium 7 is varied so that the reflection of each pixel passes through a minimum. The layer thicknesses of the individual pixels are indicated here by the relative position of the minima. It is particularly advantageous in this context that only the indicator layer 13 need be structured, and not the metal layer 9. Consequently, only a time varying voltage 11, 11' must be applied.

What is claimed is:

1. An SPR sensor (1) comprising:
   a source (3) for coherent monochromatic electromagnetic waves (4);
   a medium (7) with a tunable index of refraction; and
   an imaging detection system (5),
   wherein the medium (7) is designed as an optical resonator (2) that has a first (25) and a second opposing end face (26), upon each of which is applied at least one coating (8, 9, 9') that is suitable for producing surface plasmon resonances, and wherein the imaging detection system (5) has a polarization device (29) and is designed such that at least one ellipsometric quantity produced by the SPR sensor (1) in the reflected part (17) of the incident coherent monochromatic electromagnetic wave (4) can be detected.

2. The SPR sensor (1) in accordance with claim 1, wherein the imaging detection system (5) is designed such that an ellipsometric phase shift generated by the SPR sensor (1) in the reflected part (17) of the incident electromagnetic wave (4) can be detected.

3. The SPR sensor (1) in accordance with claim 1, wherein the imaging detection system (5) is designed such that an ellipsometric amplitude change generated by the SPR sensor (1) in the reflected part (17) of the incident electromagnetic wave (4) can be detected.

4. The SPR sensor (1) in accordance with claim 1, wherein an optical component (6) is provided for coupling the coherent monochromatic electromagnetic waves (4) into the medium (7).

5. The SPR sensor (1) in accordance with claim 1, wherein the resonator (2) is arranged on an object holder suitable for coupling coherent monochromatic electromagnetic waves (4) into the resonator (2).

6. The SPR sensor (1) in accordance with claim 1, wherein the polarization device (29) has at least one polarization means that makes it possible to adjust the polarization state of the electromagnetic wave (4).

7. The SPR sensor (1) in accordance with claim 1, wherein the electromagnetic wave (4) has a wavelength that can be predetermined.

8. The SPR sensor (1) in accordance with claim 1, wherein the material layer (14, 14') to be detected can be applied to either of the two end faces (25, 26) of the resonator (2) as desired.

9. The SPR sensor (1) in accordance with claim 1, wherein it is possible to apply to the end faces (25, 26) of the resonator at least one indicator substance (13) upon the surface of which can be formed a material layer (14, 14') to be detected through reaction with an ambient medium (12).

10. The SPR sensor (1) in accordance with claim 1, wherein the material layer (14, 14') to be detected is located in a liquid environment in a reaction cell (27) that is located on an end face of the resonator (2) and is suitable for coupling coherent monochromatic electromagnetic waves (4) into the resonator (2).

11. The SPR sensor (1) in accordance with claim 1, wherein the material layer (14, 14') to be detected is located in a gaseous environment in a reaction cell (27) that is located on an end face of the resonator (2) and is suitable for coupling coherent monochromatic electromagnetic waves (4, 4') into the resonator (2).

12. The SPR sensor (1) in accordance with claim 1, wherein the coating on the end faces (25, 26) of the resonator (2) includes an electrically conductive layer (8, 9, 9') suitable for generating surface plasmon resonances.

13. The SPR sensor (1) in accordance with claim 1, wherein the coating on the end faces (25, 26) of the resonator (2) includes a layer system of conductive and nonconductive layers suitable for generating surface plasmon resonances.

14. The SPR sensor (1) in accordance with claim 1, wherein the medium (7) of the resonator (2) includes an optically nonlinear material with a nonlinear electrical and/or magnetic susceptibility.

15. The SPR sensor (1) in accordance with claim 1, wherein the medium (7) includes an electro-optical polymer.

16. The SPR sensor (1) in accordance with claim 1, wherein the medium (7) includes an electro-optical crystal.

17. The SPR sensor (1) in accordance with claim 1, wherein the medium (7) includes an elasto-optical material.

18. The SPR sensor (1) in accordance with claim 1, wherein the index of refraction of the medium (7) can be adjusted by the application of an electric field (11, 11').

19. The SPR sensor (1) in accordance with claim 1, wherein the index of refraction in the medium (7) can be adjusted on the basis of a nonlinear optical effect through the intensity of an electromagnetic modulating beam (28) that enters at an arbitrary angle of incidence and is additional to the coherent monochromatic electromagnetic wave (4).

20. The SPR sensor (1) in accordance with claim 19, wherein the modulating beam (28) is implemented as a laser beam.

21. The SPR sensor (1) in accordance with claim 1, wherein the index of refraction of the medium (7) can be adjusted through the effects of external mechanical forces.

22. The SPR sensor (1) in accordance with claim 1, wherein at least one of the coatings (8, 9, 9') is divided into laterally separated cells, each of which forms a separate microresonator 31.

23. The SPR sensor (1) in accordance with claim 22, wherein the index of refraction of the separate microresonators 31 can be tuned separately or together as desired.

24. The SPR sensor (1) in accordance with claim 1, wherein the source (3) that generates the electromagnetic waves (4) is designed such that the separate microresonators 31 can be excited simultaneously or individually as desired.

25. The SPR sensor (1) in accordance with claim 1, wherein the detection system (5) is designed such that the signals of the separate microresonators 31 in separate detection channels can be detected simultaneously or individually as desired.

26. The SPR sensor (1) in accordance with claim 1, wherein the medium (7) has a very low extinction.

27. The SPR sensor (1) in accordance with claim 1, wherein the resonator (2) is designed as a laser resonator and the medium (7) has a negative extinction.

* * * * *